US008128967B2

(12) United States Patent
Hara

(10) Patent No.: US 8,128,967 B2
(45) Date of Patent: Mar. 6, 2012

(54) POLYPHENOL COXIB COMBINATIONS AND METHODS

(75) Inventor: Yukihiko Hara, Tokyo (JP)

(73) Assignee: Mitsui Norin Co., Ltd., Tokyo (JP)

( * ) Notice: Subject to any disclaimer, the term of this patent is extended or adjusted under 35 U.S.C. 154(b) by 529 days.

(21) Appl. No.: 11/817,999

(22) PCT Filed: Mar. 8, 2006

(86) PCT No.: PCT/US2006/008284
§ 371 (c)(1),
(2), (4) Date: Jan. 29, 2008

(87) PCT Pub. No.: WO2006/096778
PCT Pub. Date: Sep. 14, 2006

(65) Prior Publication Data
US 2009/0028963 A1   Jan. 29, 2009

Related U.S. Application Data

(60) Provisional application No. 60/660,511, filed on Mar. 8, 2005.

(51) Int. Cl.
*A01N 65/00* (2009.01)
*A01N 59/14* (2006.01)
*A01N 36/38* (2006.01)

(52) U.S. Cl. .................. 424/725; 424/659; 424/730

(58) Field of Classification Search ................... 514/406
See application file for complete search history.

(56) References Cited

U.S. PATENT DOCUMENTS

| 5,391,568 | A | 2/1995 | Chung | |
|---|---|---|---|---|
| 6,387,883 | B1 * | 5/2002 | Abbruzzese et al. | 514/21 |
| 6,410,061 | B1 | 6/2002 | Morre et al. | |
| 6,428,818 | B1 | 8/2002 | Morre et al. | |
| 6,486,204 | B2 | 11/2002 | Waldstreicher et al. | |
| 6,552,075 | B2 | 4/2003 | Gribble et al. | |
| 6,573,290 | B1 * | 6/2003 | Love | 514/406 |
| 6,630,160 | B1 * | 10/2003 | Evans et al. | |
| 6,649,645 | B1 | 11/2003 | McKearn et al. | |
| 6,713,506 | B2 * | 3/2004 | Dou et al. | 514/450 |
| 6,902,739 | B2 * | 6/2005 | McPeak et al. | 424/442 |
| 6,953,786 | B2 | 10/2005 | Pandol et al. | |
| 2004/0053900 | A1 | 3/2004 | Masferrer | |
| 2005/0165090 | A1 * | 7/2005 | Kemberling et al. | 514/456 |

FOREIGN PATENT DOCUMENTS

| DE | 20316876 | U1 * | 3/2004 |
|---|---|---|---|
| DE | 20316876 | | 11/2004 |
| WO | 9816227 | | 4/1998 |
| WO | 2004/037015 | | 5/2004 |
| WO | 2004037015 | | 5/2004 |
| WO | 2004/105517 | | 12/2004 |
| WO | 2004105517 | * | 12/2004 |
| WO | 2005/013902 | | 2/2005 |
| WO | 2005013902 | * | 2/2005 |
| WO | 2005056032 | | 6/2005 |

OTHER PUBLICATIONS

Luber, Ronald A. et al., "Effects of Celecoxib, Polyphenon E and Rosiglitazone on Hydroxybutyl (butyl)-Nitrosamine (OH-BBN)—Induced Urinary Bladder Cancers in Female Fischer-344 Rats", Proceedings of the American Association for Cancer Research Annual Meeting, vol. 45, Mar. 2004, pp. 725-726.
Mohseni H. et al., "Cox-2 Inhibition Demonstrates Potent Anti-Proliferative effects on Bladder Cancer in Vitro", Journal of Surgical Research, vol. 119, No. 2, Jun. 15, 2004, pp. 138-142.
Dragnev Konatantin H. et al., "Lung Cancer Prevention: The Guidelines", CHEST Jan. 2003, vol. 123, No. 1 Suppl, pp. 60S-71S.
Mimoto Junko et al., "(−) Epigallocatechin Gallate Can Prevent Cisplatin-Induced Lung Tumorigenesis in A/J Mice", Carcinogenesis (Oxford), vol. 21, No. 5, May 2000, pp. 915-919.
Toshiaki, O., et al., "Cyclooxygenase-2 inhibitor prevents cisplatin-induced tumorigenesis in A/J mice dose-dependently.", Second Department of Internal Medicin, Okayama University Hospital.
Luber, R., et al., "Effects of celecoxib, polyphenon E and rosiglitazon on hydroxybutyl(butyl)-nitrosamin (OH-BBN)-induced urinary bladder cancers in female Fischer-344 rats", Proceedings of the American Association for Cancer Research Annual Meeting, vol. 45, Mar. 2004, pp. 725-726.
Mohseni, H. et al., "COX-2 Inhibition Demonstrates Potent Anti-Proliferative Effects on Bladder Cancer In Vitro", Journal of Surgical Research, vol. 119, No. 2, Jun. 15, 2004, pp. 138-142.
Dragnev, K.H., et al., "Lung Cancer Prevention: the Guidelines", CHEST, Jan. 2003, vol. 123, No. 1, pp. 60S-71S.
Mimoto, J., et al., "(−)-E[igallocatechin gallate can prevent cisplatin-induced lung tumorigenesis in A/J mice", Carcinogenesis (Oxford), vol. 21, No. 5, May 2000, pp. 915-919.

* cited by examiner

*Primary Examiner* — Sreeni Padmanabhan
*Assistant Examiner* — Timothy E Betton
(74) *Attorney, Agent, or Firm* — Fish & Associates, PC

(57) ABSTRACT

Contemplated compositions and methods utilize a combination of a polyphenol and a non-polyphenol cyclooxygenase-2 inhibitor. Preferably, the compositions are pharmaceutical and/or nutraceutical compositions and formulated in a dosage form and amount such that the polyphenol and the non-polyphenol cyclooxygenase-2 inhibitor are effective to reduce tumor incidence and/or multiplicity. In preferred aspects, the polyphenol is epigallocatechin gallate, epigallocatechin, epicatechin gallate, epicatechin, and/or a mixture of polyphenols isolated from a plant (e.g., polyphenon E), and the cyclooxygenase-2 inhibitor is rofecoxib, celecoxib, and/or valdecoxib.

20 Claims, No Drawings

POLYPHENOL COXIB COMBINATIONS AND METHODS

This application claims the benefit of our U.S. provisional patent application with the Ser. No. 60/660,511, filed Mar. 8, 2005, which is incorporated by reference herein.

FIELD OF THE INVENTION

The field of the invention is pharmaceutical agents for treatment and chemoprevention of neoplastic diseases.

BACKGROUND OF THE INVENTION

Green tea extracts and their isolated constituents have been described in numerous reports as antineoplastic agents. For example, U.S. Pat. No. 6,428,818 teaches use of green tea extracts with a specific composition as therapeutic agents against various human sarcomas and carcinomas. Green tea extract has previously also been reported to enhance the effect of certain antineoplastic agents, including adriamycin and doxorubicin (e.g., Sugiyama and Sadzuka, 1998, *Cancer Lett.* 133:19-26, or Sadzuka et al., 1998, *Clin. Cancer. Res.* 4:153-156). In these studies, green tea in combination with adriamycin inhibited tumor growth in M5076 ovarian sarcoma cells, whereas adriamycin alone did not inhibit tumor growth in those cells. Similar effects were observed with green tea extract and doxorubicin on the same cell line. Green tea extract in combination with doxorubicin also enhances the inhibitory effect on Ehrlich ascites tumors in tumor-bearing mice, presumably by increasing the concentration of doxorubicin concentration in the tumor, but not in normal tissue. Further references to antineoplastic properties of green tea extracts, and especially polyphenon E can be found in *Clin. Cancer Res.* 2003 Aug. 15; 9(9):3312-9.

In other examples, administration of a pharmacologically effective amount of EGCg has been alleged to reduce the incidence of lung cancer in a mammal (see e.g., U.S. Pat. No. 5,391,568). Moreover, EGCg has also been shown to enhance the effect of certain cancer prevention drugs in vitro. For example, EGCg was demonstrated to enhance the apoptotic effect of sulindac and tamoxifen. In that study, the authors contemplated that EGCg would increase the intracellular concentration of the drugs (Suganuma et al., 1999, *Cancer Res.* 59:44-47). Further references describe combinations of selected polyphenols (e.g., EGCG and ECG) to treat specific types of cancer as taught in U.S. Pat. No. 6,410,061.

In alternative strategies of treatment and/or prevention of cancer, cyclooxygenase-2 inhibitors (COX-2 inhibitors) are employed as therapeutic agents. For example, U.S. Pat. No. 6,486,204 teaches use of certain COX-2 inhibitors drug as therapeutic agents in the treatment of prostate cancer. Similar uses of selected COX-2 inhibitors are reported in U.S. Pat. Nos. 6,552,075 and 6,649,645 in which COX-2 inhibitors are administered as anticancer drugs. Depending on the type of green tea polyphenol, COX-1 or COX-2 may be inhibited with relative good selectivity, resulting in certain therapeutic effects against bladder and prostate cancer as reported in *Am. J. Surg.* 2004 November; 188(5):505-10 or *Int. J. Cancer* 2005 Feb. 10; 113(4):660-9.

However, while at least some desirable effect can be obtained using polyphenols or COX-inhibitors, numerous disadvantages remain. Among other things, bioavailability of polyphenols is relatively low as compared to effective in vitro concentrations. Moreover, COX-2 inhibitors tend to have limited effect, unless administered at relatively large dosages. High dosages, however, were recently reported to be implicated in adverse cardiac events.

Thus, while numerous compositions and methods for pharmaceutical agents for treatment and chemoprevention of neoplastic diseases are known in the art, all or almost all of them, suffer from one or more disadvantages. Therefore, there is still a need for improved pharmaceutical agents for treatment and chemoprevention of neoplastic diseases.

SUMMARY OF THE INVENTION

The present invention is directed to compositions and methods in which a polyphenol and a non-polyphenol cyclooxygenase-2 (COX-2) inhibitor are provided, most typically as a therapeutically effective combination. Such combinations are preferably formulated such that an antineoplastic effect of the polyphenol is enhanced by the non-polyphenol cyclooxygenase-2 inhibitor (and/or vice versa).

Therefore, in one aspect of the inventive subject matter, a pharmaceutical composition comprises at least one polyphenol (e.g., epicatechin, epicatechin gallate, epigallocatechin, and/or epigallocatechin gallate, or plant extract comprising polyphenols [e.g., polyphenon E]) in combination with a non-polyphenol cyclooxygenase-2 inhibitor (e.g., rofecoxib, celecoxib, or valdecoxib). Most preferably, the COX-2 inhibitor and the polyphenol are present in an amount effective to reduce tumor incidence and/or tumor multiplicity in a mammal (typically human), wherein especially contemplated tumors include lung, bladder, prostate, and colon cancer.

While it is generally preferred that the polyphenol and the COX-2 inhibitor are administered together in a single formulation, alternative modes and formulations are also deemed suitable (e.g., administration in separate dosage units). Regardless of the particular formulation, it is generally preferred that the composition is associated with an information that indicates that the composition is effective to reduce at least one of a tumor incidence and tumor multiplicity. Viewed from another perspective, the inventors also contemplate a nutraceutical product that comprises a polyphenol in combination with a non-polyphenol cyclooxygenase-2 inhibitor.

Consequently, in another aspect of the inventive subject matter, a method of providing a pharmaceutical or nutraceutical product includes one step in which a first and/or a second pharmaceutical composition is provided (the first pharmaceutical composition preferably comprises at least one polyphenol, and the second pharmaceutical composition comprises a non-polyphenol COX-2 inhibitor). In another step, an information is provided that instructs a person to co-administer the first and second pharmaceutical compositions.

Most preferably, the polyphenol in such methods is an isolated polyphenol, and may include epicatechin, epicatechin gallate, epigallocatechin, and epigallocatechin gallate, or a polyphenol-containing composition. Typically, polyphenol-containing compositions comprise one or more plant extracts, and most preferably polyphenon E. With respect to suitable administration, it is generally preferred that the first and second pharmaceutical compositions are co-administered in an amount effective to reduce at least one of a tumor incidence and tumor multiplicity in a mammal.

Various objects, features, aspects and advantages of the present invention will become more apparent from the following detailed description of preferred embodiments of the invention.

DETAILED DESCRIPTION

The inventors have unexpectedly discovered that the antineoplastic activity of COX-2 inhibitors can be substantially increased by combination therapy of the COX-2 inhibitors with one or more polyphenols. Remarkably, it should be noted that the increased antineoplastic effect is not only synergistic in terms of reduction of tumor incidence, but also substantially reduces the tumor multiplicity.

Therefore, in one preferred aspect of the inventive subject matter, it is contemplated that a pharmaceutical composition has at least one polyphenol in combination with a non-polyphenol cyclooxygenase-2 inhibitor. For example, an exemplary composition may include celecoxib at a single unit dose of between about 200 mg to about 800 mg in combination with EGCG at a single unit dose of between about 400 mg to about 1200 mg. Most typically, such quantities of the polyphenol and the COX-2 inhibitor are contemplated to be effective as prophylactic and/or therapeutic doses where the administration is over a period of at least three days, more typically at least seven days, and most typically at least twenty days. Among other beneficial effects, it is generally contemplated that the combination will reduce tumor incidence and/or tumor multiplicity in an amount of at least 10%, more typically at least 25%, even more typically at least 40%, and most typically at least 50% as compared to tumor incidence and/or tumor multiplicity without treatment.

However, it should be recognized that numerous polyphenols other than EGCG are also deemed suitable for use herein. Among other polyphenols, it is contemplated that appropriate compounds also include catechin (C), epicatechin (EC), gallocatechin (GC), gallocatechin gallate (GCG), epigallocatechin (EGC), and epicatechin gallate (ECG). It should further be noted that the polyphenols contemplated herein include optical isomers, chiral centers, and/or stereoisomers. Thus, and all of such forms (and mixtures thereof) are contemplated herein. While it is generally preferred that the polyphenol is provided as a single and synthetic compound (e.g., at a purity of at least 90%), combinations of two or more polyphenols are also deemed suitable. While it is generally preferred that the polyphenol is isolated from a natural source, it should be appreciated that one or more polyphenols may also be synthetic.

Where more than one polyphenol is employed in contemplated combinations, it is particularly preferred that the combination is isolated from a plant (e.g., tea plant, grape, blueberry, etc.), and most preferably from green tea. Such polyphenol isolates may be normalized to a specific EGCG content, but may also be crude extracts. For example, a typical percentage of the individual catechins various green tea extracts is 10-15% EGCg, 2-3% ECG, 2% EC, and 2-3% EGC (Suganuma et al., 1999, Can. Res. 59:44-47). In addition, numerous other compounds, including caffeine, theobromine, theophylline, and phenolic acids, such as gallic acid, may also be present as constituents of green tea in smaller quantities than the polyphenols (Ahmad et al., 1998, Nutrition and Chemical Toxicity, John Wiley and Sons, Sussex, England, pp. 301-343). Where desired, and especially where relatively high dosages are administered, the extract may be decaffeinated to at least some degree (e.g., less than 0.5 wt %, more typically less than 0.1 wt %). Among other contemplated extracts, particularly suitable polyphenol extracts include polyphenon E and polyphenon B, both of which are commercially available from Mitsui Norin Japan (1-2-9 Nishishinbashi, Minato-ku, Tokyo, 105-8427, Japan). Where desirable, polyphenol-containing plant extracts may be modified by adding and/or removing one or more constituents to yield a particular chemical composition. For example, a plant extract may be spiked with EGCg, or galloylated catechins (e.g., EC, C) may be selectively removed.

Depending on the particular chemical composition of contemplated polyphenols, the quantity of the polyphenols in a single dosage unit may vary considerably. For example, contemplated dosage units may have a polyphenol content of between about 10 mg to 50 mg, more typically between about 100 mg to about 250 mg, even more typically between about 200 mg to about 500 mg, and most typically between about 200 mg to about 1500 mg (or even higher). Similarly, it should be recognized that the polyphenol may be administered in numerous formulations, and especially preferred formulations include oral formulations in solid (e.g., polyphenol powder from tea extracts) or liquid form (e.g., liquid tea extract). There are numerous commercially available oral formulations known in the art, and all of those are deemed suitable for use herein. Furthermore, various references teach methods for preparation of polyphenol compositions (e.g., U.S. Pat. No. 6,210,679, JP 01175978, or JP 2004147508), which are all deemed suitable for use herein. Moreover, and especially where it is desired that the polyphenol concentration in a subject should be maintained at a relatively high level, suitable dosage forms include slow-release forms, high-dosage forms, and/or dosage forms for multiple daily administrations. Most typically, daily dosages will be in the range of between 50 mg to 1500 mg, and even more typically between 200 mg and 1500 mg.

With respect to suitable COX-2 inhibitors, it is contemplated that all compounds with inhibitory activity against COX-2 are deemed suitable for use herein. However, especially preferred COX-2 inhibitors are relatively selective and exhibit only low to minimal COX-1 inhibition. Therefore, particularly preferred COX-2 inhibitors include rofecoxib, celecoxib, and valdecoxib. With respect to the dosage and route of administration of suitable COX-2 inhibitors it is generally contemplated that the dosages and routes are similar or identical to those currently on the market. For example, wherein the COX-2 inhibitor is rofecoxib, preferred daily dosages are in the range of between about 12.5 mg and 250 mg (and in some cases even higher). Where the COX-2 inhibitor is celecoxib, preferred daily dosages are in the range of between about 100 mg and 600 mg (and even higher), and where the COX-2 inhibitor is valdecoxib, preferred daily dosages are in the range of between about 10 mg and 40 mg, and even higher.

Additionally contemplated exemplary compounds include those described in U.S. Pat. App. No. 2004/0053985, or 2000/30091656, and U.S. Pat. Nos. 6,239,173, or 6,083,969, and in WO2004/072057, all of which are incorporated by reference herein. Still further contemplated COX-2 inhibitors may also exhibit less specificity relative to COX-1. Thus, contemplated COX-2 inhibitors may therefore also include various salicylates (and especially acetylsalicylic acid), and boric acid complexes (see e.g., U.S. Pat. App. No. 2004/0110724). In still further alternative aspects, the non-polyphenol COX-2 inhibitor may also be an isolated compound and/or preparation from a plant, and particularly contemplated plants include those known or reported to have COX-2 inhibitory activity. For example, suitable plants include *Rosmarinus* spec., *Uncaria tomentosa*, *Hypericum* spec., *Curcuma* spec., *Zingiber* spec., *Ocimum* spec., *Vitis* spec., *Tripterygium wilfordii*, *Berberis* spec., *Morinda* spec., *Acacia* spec., and *Coptis* spec.

Most typically, the COX-2 inhibitor and the plant polyphenol are administered at the same time (e.g., most typically within several minutes, less typically within several hours) to achieve pharmaceutically effective concentrations of both compounds in serum at the same time. Therefore, in further preferred aspects of the inventive subject matter, co-administration of separate dosage forms is typically advised. Alternatively, the COX-2 inhibitor and the plant polyphenol may also be compounded into a single dosage form.

In still further contemplated and alternative aspects of the inventive subject matter, a nutraceutical product may comprise a polyphenol in combination with a non-polyphenol cyclooxygenase-2 inhibitor, wherein at least one of the polyphenols and the non-polyphenol cyclooxygenase-2 inhibitor is prepared from a plant. Most typically, the polyphenol and the COX-2 inhibitor are both prepared from a plant, and compounded with a solid or liquid comestible carrier. For example, the polyphenol preparation may be isolated from green tea or black tea (e.g., preferably as commercially available composition, and especially as polyphenon E or polyphenon B). With respect to the daily dosage of the polyphenols, the same considerations as provided above apply. Thus, the nutraceutical product may include between 50 and 1500 mg of green tea polyphenols, more typically between 200 mg and 1200 mg, and most typically between 250 and 100 mg of green tea polyphenols.

In preferred aspects of such compositions, the non-polyphenol COX-2 inhibitor may be a plant extract that is prepared from *Curcuma* spec., *Zingiber* spec., and other plants known to exhibit COX-2 inhibition, or a synthetic or isolated ingredient from such plants. Exemplary ingredients include ascorbate, silymarin, vitamin E, gamma linoleic acid, omega-3-fatty acids, vanilloids, including curcumin, gingerol, shogaol, paradol, etc., which are typically present in a single dosage unit in an amount of between about 1-1000 mg, more typically between 10-500 mg, and most typically between 100-400 mg.

Nutritional products may be in all known forms, and it should be recognized that the polyphenol and the COX-2 inhibitor may be administered together in a single product, or separately as two distinct products. For example, suitable nutritional products include those having additional nutritionally useful ingredients (e.g., snack bar, beverage, multivitamin, or other fortified food product [e.g., cereal]), and those in which the polyphenol and/or COX-2 inhibitor is/are the principal active ingredient (e.g., in form of powder, syrup, tablet, capsule, etc.).

Therefore, the inventors also contemplate a method in which a pharmaceutical or nutraceutical product is provided, wherein such methods include a step of providing at least one of a first and second pharmaceutical composition, wherein the first pharmaceutical composition comprises at least one polyphenol (e.g., epicatechin, epicatechin gallate, epigallocatechin, or epigallocatechin gallate), and wherein the second pharmaceutical composition comprises a non-polyphenol cyclooxygenase-2 inhibitor (e.g., rofecoxib, celecoxib, valdecoxib, or plant extract). In another step, information is provided that instructs or informs a person to co-administer the first and second pharmaceutical compositions.

It should be appreciated that co-administration of the polyphenol and the COX-2 inhibitor in contemplated methods includes all manners of administration of the polyphenol and the COX-2. For example, the compounds may be simultaneously administered in a single dosage unit (e.g., as snack bar or orally administered dietary supplement [e.g., capsule]), or individually at approximately the same time (e.g., as two separate capsules). On the other hand, co-administration may also be in a manner in which the polyphenol is administered at one point in time, and the COX-2 inhibitor is administered at a second point in time (e.g., separated by more than 15 minutes, more than 1 hour, or even more) so long as serum concentrations of both compounds are measurable at the same time. Coadministration is preferably at a dosage effective to reduce at least one of tumor incidence and tumor multiplicity (e.g., lung, colon, bladder, or prostate cancer).

With respect to the information, it is preferred that the information that is provided may be in displayed, printed, or otherwise visually presented form (e.g., in a sales flyer, an Internet advertisement, etc.). Alternatively, or additionally, the information may also be in an audible format, including radio advertisements, talk shows, infomercials, etc.). Most preferably, the information is in printed format and associated with the pharmaceutical and/or nutraceutical product. For example, the information may be provided as a packaging insert, or be printed on the container that includes the pharmaceutical and/or nutraceutical product. In further contemplated aspects, the information may further provide information that the combination is effective as a preventative or even therapeutic agent in the treatment of a neoplastic disease, and especially in the prevention or reduction of tumor incidence and/or multiplicity.

Experiments

Administration of Contemplated Polyphenols

As already discussed above, numerous isolated and/or synthetic polyphenols may be administered, however, in especially preferred aspects, a mixture of polyphenols isolated from green tea is employed. Most preferred polyphenol mixtures are commercially available as polyphenon E by Mitsui Norin, Among numerous alternative dosages and formulations for oral administration, preferred dosages and administration schedules are described in *Clin. Cancer Res.* 2003 Aug. 15; 9(9):3312-9, which is incorporated by reference herein.

Administration of Contemplated COX-2 Inhibitors

Similarly, it is contemplated that various COX-2 inhibitors may be administered at various dosages and schedules. However, in especially preferred aspects, COX-2 inhibitors are administered at dosages and schedules ordinarily prescribed by a physician in the treatment of an inflammatory diseases (e.g., celecoxib and rofecoxib at daily dosages of 200 to 800 mg and 12.5 to 50 mg, respectively). Most preferably, and where tolerated, dosages are adjusted to highest tolerated amounts.

Effect of Cox-2 Inhibitors in Combination with EGCG or Polyphenon E on Cisplatin-Induced Lung Tumor Incidence and Multiplicity in A/J Mice Risks of secondary lung cancer in patients with non-small and small cell lung cancer are estimated to be 1-2% and 2-10% per patient per year, respectively. Cisplatin is widely used in the treatment of lung cancer and is also known as a carcinogen in experimental animals. We have recently reported that (−)-epigallocatechin gallate or the COX-2 inhibitor, celecoxib, partially inhibits cisplatin-induced lung tumors in A/J mice when administered as individual compounds (*Carcinogenesis.* 21(5): 915, 2000; Proc AACR 44 #4920: 981, 2003). However, a combination of these and other compounds had not been performed/published. The results of combination treatments are provided below in the respective sections of Experiment 1 and 2 below.

Experiment 1

Among other models investigated (data not shown), A/J mice were used to evaluate the effects of oral administration of Celecoxib in combination with EGCg or Polyphenon E on cisplatin-induced carcinogenicity. Remarkably, Cisplatin is widely used in the treatment of human lung cancer, however, is also known as a potent carcinogen in various animals.

The results are summarized in Table 1 in which CDDP refers to animals treated with Cisplatin, CDDP+EGCg refers to animals treated with Cisplatin followed by treatment with EGCG, and in which CDDP+EGCg+Cox (number) refers to animals treated with Cisplatin, EGCg, and Celecoxib. Similarly, CDDP+Cox (number)+Polyphenon E refers to animals treated with Cisplatin, Polyphenon E, and Celecoxib. Each group of animals had 10 mice.

TABLE 1

| GROUP | COMPOSITION | INCIDENCE | MULTI-PLICITY |
|---|---|---|---|
| 1 | CDDP | 0.9 | 2.2 |
| 2 | CDDP + EGCg | 0.8 | 1.2 |
| 3 | CDDP + Cox 150 | 0.9 | 2.1 |
| 4 | CDDP + Cox 1500 | 0.91 | 1.91 |
| 5 | CDDP + Cox 150 + EGCg | 0.82 | 1.64 |
| 6 | CDDP + Cox 1500 + EGCg | 0.64 | 1.18 |
| 7 | CDDP + Cox 150 + Polyphenon E | 0.7 | 1.7 |
| 8 | CDDP + Cox 1500 + Polyphenon E | 0.75 | 1.25 |

As control, A/J mice were treated with CDDP using standard protocols well known in the art and as further described below. Out of 10 mice, 9 mice (90%) developed tumors, and the average multiplicity was 2.2.

Treatment with EGCg alone (see below) was performed in the animals of group 2. Here, 80% of the mice developed tumors at a significantly reduced multiplicity (45% less than control). Low-dose and high-dose effects of Celecoxib were tested in groups 3 and 4 in which the COX-2 inhibitor was mixed with the diet at a concentration of either 150 ppm or 1,500 ppm as indicated by the numbers in parentheses (see below). Here, tumor suppression as well as multiplicity appears insignificant in both dose groups and statistically not different from the control group.

The effect of EGCg in combination with high- and low-dose COX-2 inhibitor was tested in groups 5 and 6 (see below). Remarkably, at higher dosages of celecoxib, the combination with EGCg substantially reduced tumor incidence and multiplicity (90% to 64% and 2.2 to 1.18) at statistically significant level. At lower doses of Celecoxib, the combination with EGCg moderately reduced tumor incidence and multiplicity (90% to 82% and 2.2 to 1.64) at statistically significant level. For these experiments, EGCg was dissolved in drinking water at 0.1% (wt/vol) concentration. Interestingly, EGCg alone could not significantly reduce tumor incidence, but reduced tumor multiplicity by almost 50%.

The effect of Polyphenon E in combination with high- and low-dose COX-2 inhibitor was tested in groups 7 and 8 (see below). Remarkably, at higher dosages of Celecoxib, the combination with Polyphenon E moderately reduced tumor incidence and multiplicity (90% to 70% and 2.2 to 1.7) at statistically significant level. At lower doses of Celecoxib, the combination with Polyphenon E reduced tumor incidence and multiplicity (90% to 75% and 2.2 to 1.12) at statistically significant level. For these experiments, Polyphenon E was dissolved in drinking water at 0.17% concentration.

Experiment 2

In this study, female A/J mice (4 weeks old) were divided into seven groups: group 1, no treatment; group 2, low-dose celecoxib (150 mg/kg diet); group 3, high-dose celecoxib (1500 mg/kg diet); group 4, 0.1% EGCG+low-dose celecoxib treatment (150 mg/kg diet); group 5, 0.1% EGCG+high-dose celecoxib (1500 mg/kg diet); group 6, 0.17% polyphenon E+low-dose celecoxib (150 mg/kg diet); group 7, 0.17% polyphenon E+high-dose celecoxib (1500 mg/kg diet). All mice were treated with cisplatin (1.62 mg/kg of body weight, i.p.) once a week for 10 weeks from 7 to 16 weeks of age. Mice in groups 2, 3, 4, 5, 6, and 7 were exclusively fed experimental diet prepared by mixing celecoxib. EGCG and polyphenon E were provided in drinking water. Seven groups of mice were killed at 26 weeks after treatment. The results of this experiment are presented below in Table 2.

TABLE 2

| GROUP | COMPOSITION | INCIDENCE | MULTI-PLICITY |
|---|---|---|---|
| 1 | CDDP | 95% | 2.2 |
| 2 | Cox 150 | 95% | 2.1 |
| 3 | Cox 1500 | 85.7% | 1.7 |
| 4 | Cox 150 + 0.1% EGCg | 71.4% | 1.4 |
| 5 | Cox 1500 + 0.1% EGCg | 66.7% | 1.3 |
| 6 | Cox 150 + 0.17% Polyphenon E | 80% | 2.0 |
| 7 | Cox 1500 + 0.17% Polyphenon E | 65% | 1.1 |

Similarly as in experiment 1 above, tumor incidence and multiplicity (a number of tumors/mouse, mean±SD) were 95% (19/20) and 2.2±1.5 in group 1, 95% (19/20) and 2.1±1.3 in group 2, 85.7% (18/21) and 1.7±1.2 in group 3, 71.4% (15/21) and 1.4±1.2 in group 4, 66.7% (14/21) and 1.3±1.4 ($p<0.05$ when compared to group 1) in group 5, 80% (16/20) and 2.0±1.4 in group 6, and 65% (13/20) and 1.1±0.1 ($p<0.05$ when compared to group 1) in group 7.

Thus, the data strongly suggest that COX-2 inhibitors when combined with EGCG show a synergetic chemopreventive and therapeutic effect in mice. Celecoxib when combined with EGCG or polyphenon E significantly reduced tumor incidence as well as multiplicity in mice treated by cisplatin. In addition, low-dose celecoxib significantly prevented cisplatin-induced weight loss ($p<0.05$). These findings suggest celecoxib when combined with EGCG or polyphenon E can more efficiently inhibit cisplatin-induced tumorigenesis.

Thus, specific embodiments and applications of combinations of plant polyphenols and COX-2 inhibitors have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:
1. A pharmaceutical composition comprising at least one green tea polyphenol in combination with a non-polyphenol cyclooxygenase-2 (COX-2) inhibitor, wherein the composition comprises an effective amount of the polyphenol and the

COX-2 inhibitor to reduce tumor incidence in a mammal, wherein the polyphenol is selected from the group consisting of epigallocatechin gallate and polyphenon E, wherein the non-polyphenol COX-2 inhibitor is selected from the group consisting of rofecoxib, celecoxib, and valdecoxib, and wherein the combination of the polyphenol and the COX-2 inhibitor are present in amounts of between 50 and 1500 mg and between 1 to 1000 mg, respectively, that are effective to achieve a synergistic effect to reduce tumor incidence and multiplicity in an amount of at least 10% as compared to tumor incidence and multiplicity without treatment.

2. A pharmaceutical composition comprising at least one green tea polyphenol in combination with a non-polyphenol cyclooxygenase-2 (COX-2) inhibitor, wherein the composition comprises an effective amount of the polyphenol and the COX-2 inhibitor to reduce cancer incidence in a mammal, wherein the polyphenol is selected from the group consisting of epigallocatechin gallate and polyphenon E, wherein the non-polyphenol COX-2 inhibitor is selected from the group consisting of rofecoxib, celecoxib, and valdecoxib, and wherein the polyphenol and the COX-2 inhibitor are present in amounts of between 50 and 1500 mg and between 1 to 1000 mg, respectively, that are effective to achieve a synergistic effect to reduce tumor incidence and multiplicity in an amount of at least 10% as compared to tumor incidence and multiplicity without treatment.

3. A pharmaceutical composition comprising at least one polyphenol in combination with a non-polyphenol cyclooxygenase-2 (COX-2) inhibitor, wherein the polyphenol is selected from the group consisting of epigallocatechin gallate and polyphenon E, wherein the non-polyphenol COX-2 inhibitor is selected from the group consisting of rofecoxib, celecoxib, and valdecoxib, and wherein the polyphenol and the COX-2 inhibitor are present in amounts of between 50 and 1500 mg and between 1 to 1000 mg, respectively, that are effective to achieve a synergistic effect to reduce tumor incidence and multiplicity in an amount of at least 10% as compared to tumor incidence and multiplicity without treatment.

4. The pharmaceutical composition according to claim 1, wherein the amount of the polyphenol and the COX-2 inhibitor is effective to reduce tumor multiplicity in a mammal.

5. The pharmaceutical composition according to claim 2, wherein the amount of the polyphenol and the COX-2 inhibitor is effective to reduce cancer multiplicity in a mammal.

6. The pharmaceutical composition of any one of claim 1, 2, 3, 4, or 5 wherein the cyclooxygenase-2 inhibitor is celecoxib.

7. The pharmaceutical composition of claim 6 wherein the polyphenol is selected from the group consisting of epicatechin, epicatechin gallate, epigallocatechin, and epigallocatechin gallate.

8. The pharmaceutical composition of any one of claim 1, 2, 3, 4, or 5 wherein the cyclooxygenase-2 inhibitor is in a dosage suitable for administration of between about 5 mg and 500 mg per day, and wherein the polyphenol is in a dosage suitable for administration of between about 50 mg and 1500 mg per day.

9. The pharmaceutical composition of claim 8 wherein the tumor incidence in the mammal is lung cancer incidence.

10. The pharmaceutical composition of claim 8 wherein the tumor multiplicity in the mammal is lung cancer multiplicity.

11. The pharmaceutical composition of claim 1 further comprising an information that is associated with the composition and that indicates that the composition is effective to reduce at least one of a tumor incidence and tumor multiplicity.

12. The pharmaceutical composition of any one of claim 1, 2, 3, 4, or 5 wherein the at least one polyphenol and the cyclooxygenase-2 inhibitor are formulated in separate dosage units.

13. The pharmaceutical composition of any one of claim 1, 2, 3, 4, or 5 wherein the at least one polyphenol is present in the composition as part of a mixture of chemically distinct polyphenols.

14. The pharmaceutical composition of claim 13 wherein the mixture of chemically distinct polyphenols comprises at least one synthetic polyphenol.

15. The pharmaceutical composition of claim 14 wherein the mixture of chemically distinct polyphenols comprises polyphenon E.

16. The pharmaceutical composition of any one of claim 1, 2, or 3 wherein the COX-2 inhibitor is celecoxib.

17. A nutraceutical product comprising a green tea polyphenol in combination with a non-polyphenol cyclooxygenase-2 inhibitor, and a nutraceutically acceptable carrier, wherein the polyphenol is selected from the group consisting of epigallocatechin gallate and polyphenon E, wherein the non-polyphenol COX-2 inhibitor is selected from the group consisting of gamma linoleic acid, an omega-3 fatty acid, silymarin, gingerol, paradol, acetylsalicylic acid, and a boric acid complex, and wherein the polyphenol and the COX-2 inhibitor are present in amounts of between 50 and 1500 mg and between 1 to 1000 mg, respectively, that are effective to achieve a synergistic effect to reduce tumor incidence and multiplicity in an amount of at least 10% as compared to tumor incidence and multiplicity without treatment.

18. The nutraceutical product of claim 17 wherein the polyphenol is present in the product as part of a mixture of chemically distinct polyphenols.

19. The nutraceutical product of claim 17 wherein the mixture of chemically distinct polyphenols comprises polyphenon E.

20. The nutraceutical product of claim 17 wherein the cyclooxygenase-2 inhibitor is at least one of an extract of a plant selected from the group consisting of *Rosmarinus* spec, *Uncaria tomentosa*, and *Hypericum* spec, and a compound selected from the group consisting of ascorbate, silymarin, vitamin E, gamma linoleic acid, and an omega-3-fatty acid.

* * * * *